United States Patent [19]

Giampapa

[11] 4,048,444
[45] Sept. 13, 1977

[54] PHONOSTETHOSCOPE CONVERSION UNIT FOR AMPLIFICATION AND CLARIFICATION OF CORPOREAL SOUNDS

[76] Inventor: Vincent C. Giampapa, 47 Addison Drive, Fairfield, N.J. 07006

[21] Appl. No.: 605,047

[22] Filed: Aug. 15, 1975

[51] Int. Cl.² .......................... H04R 1/46; A61B 7/04
[52] U.S. Cl. .................................................. 179/1 ST
[58] Field of Search ............ 179/1 ST, 107 R, 107 E, 179/156 R, 156 A, 182 R, 182 A

[56] References Cited

U.S. PATENT DOCUMENTS

| 3,247,324 | 4/1966 | Cefaly et al. | 179/1 ST |
| 3,396,241 | 8/1968 | Anderson et al. | 179/1 ST |
| 3,493,695 | 2/1970 | Stork | 179/107 R |
| 3,846,585 | 11/1974 | Slosberg | 179/1 ST |
| 3,894,196 | 7/1975 | Briskey | 179/107 FD |

Primary Examiner—Kathleen H. Claffy
Assistant Examiner—E. S. Kemeny
Attorney, Agent, or Firm—James F. Cottone

[57] ABSTRACT

A phonostethoscope conversion unit for use with conventional stethoscopes in order to amplify and clarify critical body sounds by interposing a pair of detachable electronic conversion units at the earpiece locations to optionally provide improved operational characteristics. The electronic units are located at the terminal end of the vibrating air column so as to provide an amplified version of the sounds of interest in a manner which the user has been attuned by experience to expect from his instrument, and further to minimize the impact of the units during stethoscope usage when the electronic assist capability is not in use.

4 Claims, 7 Drawing Figures

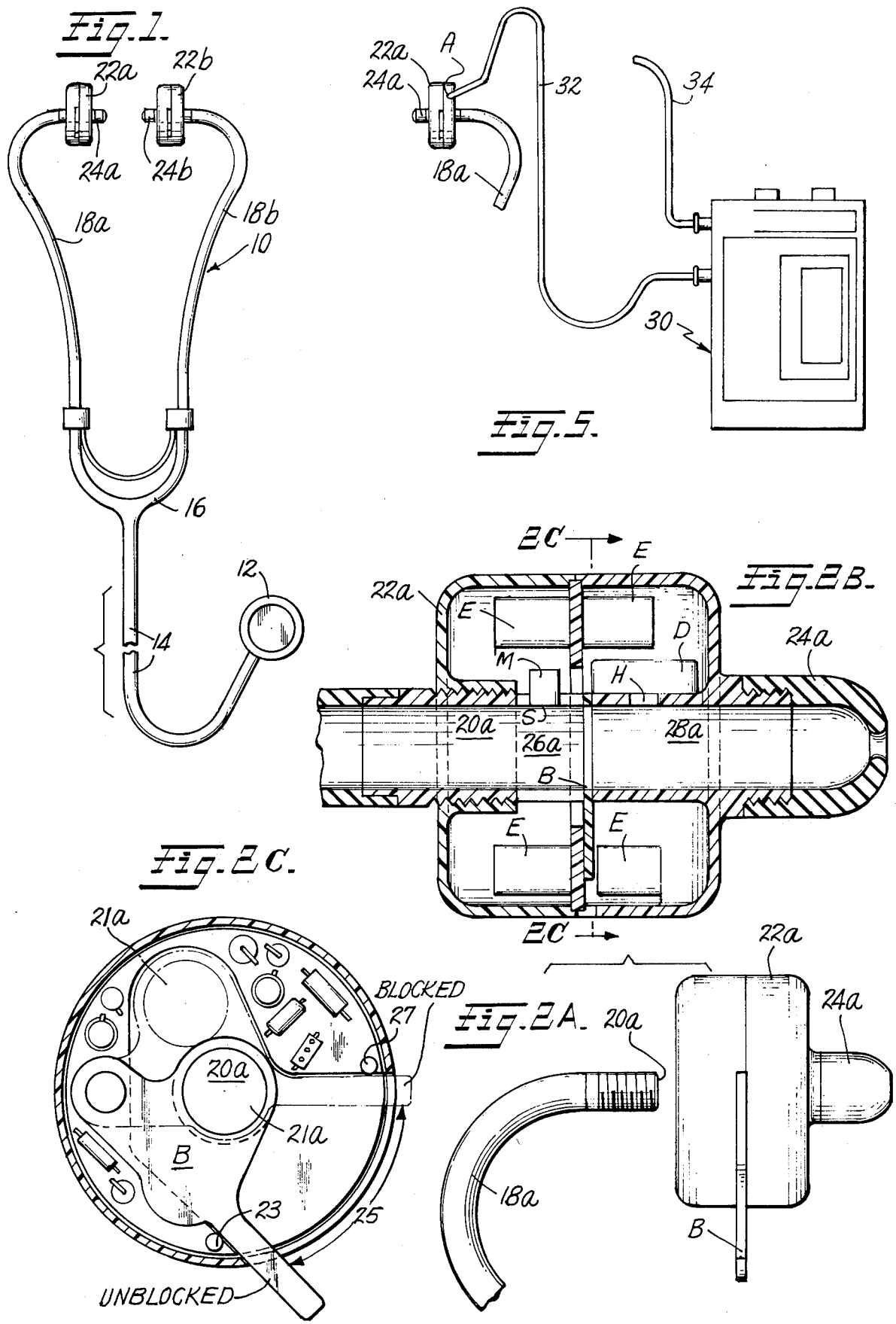

PHONOSTETHOSCOPE CONVERSION UNIT FOR AMPLIFICATION AND CLARIFICATION OF CORPOREAL SOUNDS

BACKGROUND OF THE INVENTION

This invention relates to electronically assisted stethoscopes, and more particularly to electronic conversion units for converting a conventional stethoscope into a phonostethoscope whose authenticity of sound amplification and ease of operation are within range of those directly and indirectly involved with the medical field.

It is common procedure during the workup of a patient to include electrocardiogram recordings in the patient's chart. Such a recording provides evidence of important cardiac functions; rate, rhythm, axis hypertrophy, and miscellaneous drugs effects. Unfortunately the attempt to solve problems of cardiac defects, valvular hemodynamics, and other physiological abnormalities are often limited by the individuals acoustic capacity and memory. Specialized equipment is available to aid this aural registering, including a variety of electronic recording and analysis devices. However these devices are often expensive, non-mobile and require the services of trained personnel.

Conventional stethoscopes often employ a resonant peak within their frequency response characteristics, this peak often falling nominally between 50 Hz and 200 Hz. Certain stethoscope models exhibit peaks in their response at 1500 Hz to 3000 Hz. These characteristics are determined by a number of factors. Among the major contributors to resonant peaks are chestpiece chamber volume and diaphragm thickness/mass ratio. These resonant peaks are often highly useful in that they are utilized by physicians to accentuate certain commonly encountered sounds.

Electronic stethoscopes have been available for many years but they have not gained wide acceptance by medical practitioners because of their inconveniences in use, their high cost, high weight and bulk, difficulty in attachment, and often lack of easy mobility. Additionally, and perhaps more importantly, the electronic stethoscopes previously available have imposed a burden on the user in the form of a highly unnatural sounding instrument, or at best, an instrument to which the user has not been attuned. Representative prior art includes Slosberg et al U.S. Pat. Nos. 3,846,585, Keesee 3,539,724, Minsky 2,385,221, Cefaly et al 3,247,324, Clark et al 3,182,129, Croslin 3,233,041, and Andries et al 3,160,708, each of which fails to recognize the importance of providing a light weight transducer assembly easily mountable and located at the earpiece locations which is the terminal point of exit of the sound from the air column.

The prior art devices may be viewed as utilizing techniques of basically three general types. The first type utilizes an electronic input sensor and amplification device at the chestpiece location, and thereafter employs purely passive acoustic means throughout the length of the vibrating air column and into the earpieces. A second type utilizes a combined electronic input sensor and amplification means at some intermediate point in the vibrating air column; while the input sensor and the output means are of conventional acoustic configurations. The third type utilizes electronic amplification techniques at both the chestpiece and at some intermediate point within the vibrating air column, while the earpieces remain conventional.

I have discovered that the location of the amplification and frequency controls in the prior art devices has not resulted in optimal positioning of the devices and in turn have often created additional problems.

Considering the stethoscope and the human body as an integral unit for transmission of sounds, it becomes apparent that whatever form of amplification, or frequency response shaping that interrupts the sound flow along its route from origin to exit of the stethoscope, it will invariably cause alterations in sound characteristics. More importantly, it often alters the character of the perceived sound as the physician has been trained to recognize it. To alleviate this situation, this invention utilizes the concept of placing the amplifier unit and frequency response shaping elements at the final exit of the sound from the stethoscope (i.e., earpieces) resulting in substantially unaltered sound flow, and a highly natural sounding electronically assisted stethoscope.

It will become obvious that this new combination and configuration has advantages over existing electronically aided stethoscopes and may be of significant aid in diagnostic and teaching situations when utilized in conjunction with a specific recording format and presently existing medical procedures.

SUMMARY OF THE INVENTION

It is therefore a primary object of the instant invention to overcome the disadvantages of the prior art by providing the benefits of electronic assistance to existing, conventional air-column actuated stethoscopes in the form of conversion units adaptable to most stethoscope models in wide-spread use.

It is another object of this invention to provide an electronically assisted stethoscope, hereinafter referred to as a photostethoscope, that combines the advantages of conventional acoustic listening with those obtainable via electronic amplification and frequency response shaping.

It is another object of this invention to provide a dual mode capability, purely acoustic or acoustoelectronic, by means of a pair of light weight, low cost, easily attached conversion units.

It is another object of this invention to provide a complete photostethoscope to aid the diagnostic acuity of those physicians or other users having hearing deficiencies.

It is yet another object of the instant invention to provide an electronic conversion unit which, when not in active use, does not alter the design or operational characteristics of the vibrating air column of the basic stethoscope.

It is yet another object of this invention to provide means for permanent recording of a variety of physiological body sounds to be later utilized as diagnostic aids.

It is still another object of the present invention to provide means for amplified and recorded outputs of significant or unique physiological sounds for use as teaching aids.

It is yet another object of this invention to provide an electronic assist for use with stethoscopes being used in a high ambient noise area.

It is yet another object of this invention to provide an electronic conversion unit which can be fitted onto a standard stethoscope without the use of any tools, needs no calibration or special retraining for the physician.

It is still another objective of this invention to provide a phonostethoscope which allows for the rapid selection of a plurality of amplification ratios and frequency responses to cover a wide range of operating requirements.

It is a further object of this invention to provide means for a new stethoscopic diagnostic procedure by using a separate electronic unit to deliver to each ear different amplitudes and frequencies optimized for diverse corporeal sounds and enabling the physician to conceptually combine these sounds into a composite picture of physiological phenomena being investigated.

BRIEF DESCRIPTION OF THE DRAWINGS

Other objects and features of the invention will become more readily understood from the following detailed description when read in conjunction with the accompanying drawings in which like reference numerals designate like parts throughout the figures thereof, and wherein;

FIG. 1 is an overall view of a stethoscope showing the interconnections of the electronic conversion units of the instant invention;

FIG. 2 comprised of 2A-2C illustrates the general mechanical configuration and internal arrangement of an electronic conversion unit;

FIG. 5 illustrates the photostethoscope being used in conjunction with permanent recording means.

DETAILED DESCRIPTION OF THE PREFERRED EMBODIMENT

Figure 3:
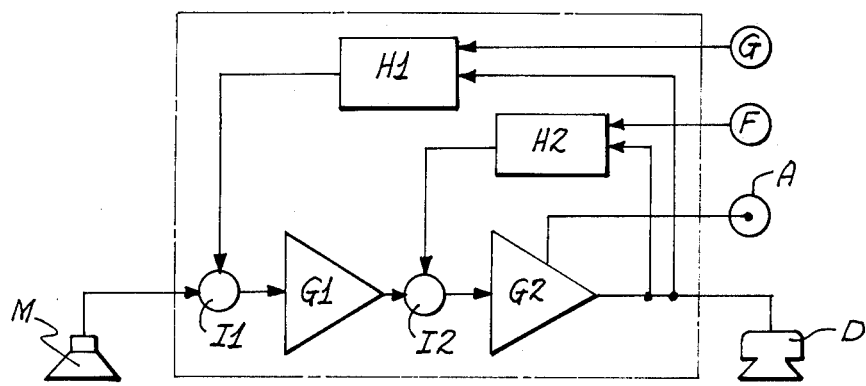
FIG. 3 illustrates the electronics amplifying circuitry in functional block form.

Referring to FIG. 1, a preferred embodiment of an electronically assisted stethoscope indicated generally at 10 in FIG. 1. The assembly includes an acoustic chestpiece member 12, a flexible tubular connecting member 14, a neck region 16 which provides for sound division and transmission to two ear branch tubular members 18a and 18b. Each ear branch member 18a terminates in an output aperture 20a (shown in FIG. 2A). Hereinafter the "a" branch is described; the "b" branch is identical. For a conventional stethoscope the variations in sound pressure level induced in the chestpiece due to the physiological phenomena under investigation are conducted via the air columns within the flexible tubular connecting member 14 and the two ear branch tubular members 18A and 18B into the ear of the user physician for analysis and interpretation. In addition to the conventional passive, vibrating air column stethoscope, a pair of electronic conversion units 22a and 22b are connected to each of the two ear branches thus providing binaural, electronically assisted representation of the physiological sounds of interest. The output of the electronic conversion units 22a and 22b are routed to the user's ears via eartip pieces 24a and 24b respectively.

FIGS. 2A-2C illustrate the mechanical configuration of the electronic conversion unit 22a in greater detail. As shown in FIG. 2A, a preferred embodiment of the present invention allows for the rapid conversion of a conventional stethoscope merely by the removal of the earpiece tip 24a, connection of an electronic conversion unit 22a onto the output aperture 20a of an ear branch member 18a, and the reconnection of the earpiece tip 24a onto the threaded output aperture of the electronics conversion unit 22a. Obviously, the above steps may be accomplished in a more or less permanent manner by use of adhesives of various degrees of permanence thereby rendering the resulting instrument an integrated phonostethoscope rather than a convertible device.

FIG. 2B shows a cross sectional view of the electronic conversion unit 22a, and more particularly the internal arrangement of selected portions of the electronics. A collection of discrete components comprising the amplifying circuitry (shown in functional block form in FIG. 3) are housed on a printed circuit board so as to occupy a volume nominally that of an elongated annulus, as indicated by a region designated E. Included in this collection of components are a plurality of components (shown in generalized form in FIG. 2C) consisting of: transistors, diodes, resistors, capacitors, batteries, switches and other elements to implement the conventional amplifier and feedback networks as are well known to those skilled in the electronics instrumentation art. An input microphone M is located adjacent to the sound channel and receives its stimulus via a plurality of vent slots S in the portion of the electronic conversion unit 22a which constitutes a uniform continuation of the stethoscope air column, the primary air column 26a, fed by the output aperture 20a. A sound baffle B is located so as to provide a movable blockage of the primary air column as described below. Earpiece driver D is located so as to also communicate with the air column but in a position beyond the sound baffle B into a secondary air column 28a. The acoustic output of earpiece driver D is delivered into the secondary air column 28a via a plurality of holes designated as H.

FIG. 2C is a cross sectional view of electronics conversion unit 22a, taken along the lines - 2C -, to illustrate the operation and function of sound baffle B. The sound baffle B, a flat, rigid member, is activated through a 70° arc 25 to substantially block the primary air column when the electronically assisted capability is in use. The sound baffle B is shown first in the unblocked position where it is restrained by a stop pin 23. At this location, a circular aperture 21a in sound baffle B is aligned with the continuation of aperture 20a of earpiece member 18a so as to provide unimpeded sound transmission to the ear of the user via primary air column 26a, secondary air column 28a and eartip piece 24a. The sound baffle B is also shown in phantom lines in the blocked position, after it has been actuated through the arc 25 (nominally 70°) where it is restrained by a stop pin 27. As shown, the aperture 21a in sound baffle B no longer aligns with aperture 20a, and the solid portion of sound baffle B blocks the air column, thereby producing the substantially independent and acoustically isolated secondary air column 28a. The baffle actuation is coupled to an on/off microswitch (not shown) so as to energize the electronics circuitry whenever the sound transmission path is divided into the primary and secondary air column 26a 28a. This arrangement provides the required input/output isolation, thus precluding unwanted electronic oscillations. Such features as an access cover for battery replacement, means for the selection, via discrete switch positions and/or continuously variable control means, of amplifier gains and frequency response, and an output connection for recording purposes are not discussed as they are in common usage in the electronic art.

Referring now to FIG. 3, a circuit for providing the required electronic amplification and frequency response shaping is illustrated. The circuit has as its input transducer the microphone M for the conversion of incident sound pressure variations into corresponding electrical analog voltages. The output of microphone M is applied via an input node I1 to the input of a preamplifier G1 and in turn via an input node I2 to the input of a power amplifier G2. A feedback network H2 is connected from the output of power amplifier G2 back to input node I2 to provide a frequency selective return path. The feedback network H2 functions to shape the overall system frequency response so as to produce the three characteristic frequency response curves which will be descibed below in connection with FIG. 5. A second feedback network H1 is connected from the output of power amplifier G2 back to the input of preamplifier G1 via input node I1. This second feedback network functions to establish the overall amplification provided by the electronic amplifier unit. An adjustment control G is provided to select overall system amplification by altering elements in the network H1, and an adjustment control F performs a similar function in concert with the network H2 for overall system frequency response. These adjustments are substantially independent, are well known in the electronics arts, and are described in more functional detail hereinbelow. An output of power amplifier G2 is routed to the ear piece driver D thereby providing an acoustical output representative of the lower level acoustic input as sensed by microphone M. A further output from power amplifier G2 is applied to an auxiliary output terminal A for use with recording devices or other external equipment.

Figure 4:
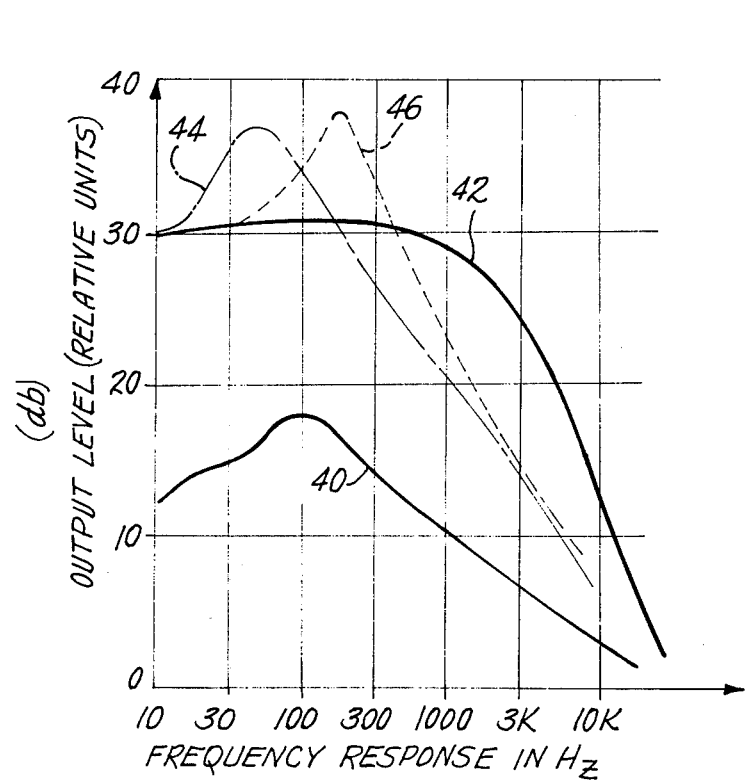
FIG. 4 shows the amplitude/frequency response curves associated with various stethoscope configurations disclosed herein.

Referring now to FIG. 4, a number of amplitude-frequency response curves are shown for a single electronics channel. The curves represent the overall acoustic response of a conventional stethoscope equipped with the electronic conversion units, for various operating modes. A curve 40 illustrates the response of the system with the electronic units inoperative. This is substantially the same as would be encountered in a Basic unequipped stethoscope and is expressed in decibels (db) where the zero db level has been arbitrarily selected to facilitate comparisons with other curves. The curve 40 shows a fairly broad resonant peak in the vicinity of 100–200 Hz, the output drops off sharply thereafter with increasing frequency. A curve 42 shows the overall response of the electronically-assisted stethoscope when the unit is operated with "FLAT" amplification. Curve 42 is nominally 15-20 db greater than the BASIC system and is flat within ± 1 db for the frequency range of 10 Hz to 1,000 Hz. Curves 44 and 46 show the resulting responses when the electronics conversion units are adjusted in frequency to provide "PEAKED" amplification. The curve 44 shows a "LOW PEAK" response, nominally 6-8 db greater than the "FLAT" curve, with the peak located in the 20-70 Hz region, while curve 46 shows a similar peak, the "HIGH PEAK," in the 140 Hz region. Both peaked responses fall off sharply with increasing frequency beyond their peaked regions.

Curves 42–46 should be considered only representative in the sense that they show only one each of entire families of amplitudefrequency responses available for the stethoscope user. For example: other FLAT response curves similar to curve 42, are also selectable as discussed above by user selection of alternate gain adjustments of element H1, shown in FIG. 3, by means of control G. These additional FLAT curves would be everywhere parallel to curve 42 but might be typically adjustable in 3 db steps within some limited range. By way of further illustration, a three discrete position selection by control 6 of elements comprising H1 could produce the curve 42 as its MID gain position, with a HIGH gain position 3 db higher than that shown, and a LOW gain position 3 db lower than that shown. In addition, the location of the maximum frequency response peaks are also adjustable to meet the criteria of best enhancement of the corporeal sound of interest at the moment; or optimum compensation for loss of frequency acuity in the particular ear, or ears, of the user. For the illustrative modes described — three discrete gain positions (HIGH, MID and LOW), and three discrete frequency responses (FLAT, LOW PEAK and HIGH PEAK)—a total of nine distinct responses are available at each ear.

FIG. 5 illustrates a conventional two channel recording device 30 electronically coupled to output A of electronics conversion unit 22a via an interconnecting cable 32, and to a further electronic conversion unit (not shown) via an interconnecting cable 34.

While a particular embodiment has been described and illustrated in detail it will be understood that the description and drawings are merely illustrative of and not restrictive on the broad invention, and that various departures and modifications may be made without departing from the spirit and scope of the appended claims.

I claim:
1. An electronically assisted stethoscope comprising:
   a. a chestpiece member;
   b. a pair of electronic conversion units;
   c. an integral air column member connecting each of said electronic conversion units to said chestpiece member;
   wherein said pair of electronic conversion units are independently operable and are positioned at the output end of the acoustic path so as to constitute the output elements of said electronically assisted stethoscope,
   and wherein said electronic conversion units each comprise:
   a. a primary and a secondary air column;
   b. a first electroacoustic transducer means in acoustic communication with said primary air column for converting acoustic signals into corresponding electrical signals;
   c. amplifying means connected to said first electroacoustic transducer means for amplifying said electrical signals;
   d. a second electroacoustic transducer placed in acoustic communication with said secondary air column for producing amplified acoustic signals corresponding to said amplified electrical signals;
   e. an earpiece member in acoustic communication with said secondary air column; and
   f. sound baffle means movably disposed for selectively substantially acoustically isolating said primary and secondary air columns.

2. An electronically assisted stethoscope as recited in claim 1 wherein, upon movement of said sound baffle means so as to unite said primary and secondary air columns, and further to deenergize said amplifying means, the basic stethoscope's characteristic performance is realized in substantially unaltered form by virtue of an increase in acoustic path length of less than five percent due to the addition of said electronic conversion units.

3. An electronically assisted stethoscope as recited in claim 1 wherein said amplifying means comprises:
   a. a plurality of amplifier circuits;
   b. a first feedback network operative across a selected portion of said amplifier circuits to adjustably establish amplification ratios and further to stabilize said amplification ratios;
   c. a second feedback network operative across a selected portion of said amplifier circuits for adjustably shaping the overall frequency response of said amplification;
   wherein said first and second feedback networks are substantially non-interactive so as to provide a plurality of amplification ratios and frequency responses as independent degrees of freedom in each of said electronic conversion units.

4. In an electronic conversion unit for use in conjunction with a conventional air-column actuated stethoscope comprising a chestpiece member a pair of earpiece members, an integral air column member connecting said earpiece members to said chestpiece member, wherein said electronic conversion unit comprises a primary and a secondary air column, a first electroacoustic transducer means exposed to said primary air column for converting acoustic signals into corresponding electrical signals, amplifying means connected to said first electroacoustical means for amplifying said electrical signals, a second electroacoustical transducers means connected to said amplifying means and selectively exposed to said secondary air column for producing amplified acoustic signals corresponding to said electrical signals comprising: interposing one of said electronic conversion units between said integral air column member and at least one of said earpiece members at a location immediately preceding said earpiece members.

* * * * *